(12) United States Patent
Wang et al.

(10) Patent No.: US 7,662,413 B2
(45) Date of Patent: Feb. 16, 2010

(54) EXTRACTS OF SACRED WATER LOTUS FOR THE TREATMENT OF CANCER

(75) Inventors: Chau-Jong Wang, No. 110, Sec. 1, Jianguo N. Rd. South District, Taichung City (TW) 402; Mong-Yuan Yang, Taichung (TW)

(73) Assignees: Chung Shan Medical University, Taichung (TW); Chau-Jong Wang, Taichung (TW)

( * ) Notice: Subject to any disclaimer, the term of this patent is extended or adjusted under 35 U.S.C. 154(b) by 1 day.

(21) Appl. No.: 12/038,755

(22) Filed: Feb. 27, 2008

(65) Prior Publication Data

US 2009/0214683 A1 Aug. 27, 2009

(51) Int. Cl.
*A61K 36/00* (2006.01)
*A61K 9/00* (2006.01)
*A61K 47/00* (2006.01)

(52) U.S. Cl. ........................ 424/725; 424/774; 424/400; 424/439

(58) Field of Classification Search ........................ None
See application file for complete search history.

(56) References Cited

U.S. PATENT DOCUMENTS

| 7,338,671 | B2 * | 3/2008 | Golz-Berner et al. | ........ 424/725 |
| 2004/0091541 | A1 * | 5/2004 | Unger | ........................ 424/486 |
| 2006/0182823 | A1 * | 8/2006 | Yang et al. | ................... 424/757 |

* cited by examiner

*Primary Examiner*—Christopher R Tate
*Assistant Examiner*—Randall Winston
(74) *Attorney, Agent, or Firm*—WPAT, P.C.; Anthony King; Kay Yang

(57) ABSTRACT

The present invention provides *Nelumbo* extract and a method thereof. The present invention further provides a composition comprising said extract and a method for treating subject suffering from breast cancer with the composition.

6 Claims, 6 Drawing Sheets

(A)

(B)

(A)

(B)

(A)

(B)

(A)

(B)

EXTRACTS OF SACRED WATER LOTUS FOR THE TREATMENT OF CANCER

FIELD OF THE INVENTION

The present invention relates to extract of *Nelumbo nucifera* leaves and a method thereof. The present invention further relates to a composition comprising extract of *Nelumbo nucifera* leaves and its use to treat breast cancer.

BACKGROUND

Breast cancer is a cancer of the glandular breast tissue and it is developed when a cancerous tumor occurs inside the breast. There are two main types of breast cancer. One is ductal carcinoma which starts in the tubes (ducts) that move milk from the breast to the nipple; most breast cancers are of this type. The other is lobular carcinoma which starts in parts of the breast, called lobules, which produce milk. In rare cases, breast cancer can start in other areas of the breast.

Many breast cancers are sensitive to the hormone estrogen. This means that estrogen causes the breast cancer tumor to grow. Such cancer is called estrogen receptor positive cancer or ER positive cancer.

Some women have what's called HER2-positive breast cancer. HER2 refers to a gene that helps cells grow, divide, and repair themselves. When cells have too many copies of this gene, cells, including cancer cells, grow faster. Experts think that women with HER2-positive breast cancer have a more aggressive disease and a higher risk of recurrence than those who do not have this type.

Worldwide, breast cancer is the fifth most common cause of cancer death (after lung cancer, stomach cancer, liver cancer, and colon cancer). In 2005, breast cancer caused 502,000 deaths (7% of cancer deaths; almost 1% of all deaths) worldwide. Among women worldwide, breast cancer is the most common cause of cancer death. Because the breast is composed of identical tissues in males and females, breast cancer also occurs in males, though it is less common.

Several herbal compounds or complexes have been indicated to be candidate drugs for treating breast cancer. For example, Puerariae radix and Ginseng radix Rubra extracts were suggested to have effective estrogenic actions and could be developed as estrogenic supplements. In addition, folk history has it that Sacred water lotus (*Nelumbo nucifera*) can be used to treat cancer. Modern research has isolated certain compounds from the plant that show anticancer activity. However, there was no research showing that extracts of *Nelumbo nucifera* can mitigate breast cancer.

Sacred water lotus (*Nelumbo nucifera*) has been used in the Orient as a medicinal herb for well over 1,500 years. All parts of the plant are used as herbal medicine because they have astringent, cardio-tonic, febrifuge, hypotensive, resolvent, stomachic, styptic, tonic or vessel dilating effect. For example, the leaf juice is used in the treatment of diarrhoea and is decocted with liquorice for the treatment of sunstroke.

A decoction of the flowers is used in the treatment of premature ejaculation. The flowers are recommended as a cardiac tonic. A decoction of the floral receptacle is used in the treatment of abdominal cramps, bloody discharges etc. The flower stalk is haemostatic. It is used in treating bleeding gastric ulcers, excessive menstruation, post-partum haemorrhage.

The stamens are used in treating urinary frequency, premature ejaculation, haemolysis, epistasis and uterine bleeding. Besides, a decoction of the fruit is used in the treatment of agitation, fever, heart complaints etc. Furthermore, the seed is sedative and used in the treatment of poor digestion, enteritis, chronic diarrhoea, insomnia and palpitations.

The root is tonic and the root starch is used in the treatment of diarrhea or dysentery, a paste is applied to ringworm and other skin ailments. It is also taken internally in the treatment of haemorrhages, excessive menstruation and nosebleeds. The roots are harvested in autumn or winter and dried for later use.

The root nodes are used in the treatment of nasal bleeding, haemoptysis, haematuria and functional bleeding of the uterus. The plumule and radicle are used to treat thirst in high febrile disease, hypertension, insomnia and restlessness.

SUMMARY OF THE INVENTION

The present invention provides an extract which is prepared by the following steps:
(a) cutting *Nelumbo* leaves into small pieces and extracting with water;
(b) filtering the extracts through a filter paper;
(c) concentrating the filtrate by evaporation; and
(d) lyophilizing the concentrate to yield *Nelumbo* leaf extract.

The present invention also provides a method for treating a subject suffering from breast cancer, comprising administrating to the subject a pharmaceutically effective dosage of said extract.

DETAILED DESCRIPTION OF THE INVENTION

While the invention has been described and exemplified in sufficient detail for those skilled in this art to make and use it, various alternatives, modifications, and improvements should be apparent without departing from the spirit and scope of the invention.

The present invention provides an extract which is prepared by the following steps:

(a) cutting *Nelumbo* leaves into small pieces and extracting with water;

(b) filtering the extracts through a filter paper;

(c) concentrating the filtrate by evaporation; and (d) lyophilizing the concentrate to yield *Nelumbo* leaf extract.

In a preferred embodiment, the *Nelumbo* is *Nelumbo nucifera*.

The present invention further provides a method for treating a subject suffering from breast cancer, comprising administrating to the subject a pharmaceutically effective dosage of said extract.

In a preferred embodiment, the *Nelumbo* is *Nelumbo nucifera*, and the extract comprises phenolic acid or polyphenols.

In a preferred embodiment, the effective dosage of said extract reduces incidence, multiplicity, number, weight, size or volume of mammary tumors in a mammal.

In a more preferred embodiment, the effective dosage is 0.1~5% *Nelumbo* leaf extract.

In a better embodiment, the effective dosage is 0.5~2% *Nelumbo* leaf extract.

In a preferred embodiment, the extract is administrated orally and the subject is human.

EXAMPLES

The examples below are non-limiting and are merely representative of various aspects and features of the present invention.

Preparation of Extract from *Nelumbo nucifera* Leaves

*Nelumbo nucifera* leaves were harvested from Tainan in Taiwan. Then, the leaves were cleaned with water and air-dried. 20 g dried leaves were cut into small pieces and extracted with 1000 ml distilled water in 4° C. overnight. The extract was filtered through a Whatman paper No. 1, and concentrated by evaporation, and lyophilized to yield *Nelumbo* leaf extract (NLE), extract of the present invention.

Experimental Design for the Invention

Figure 1:
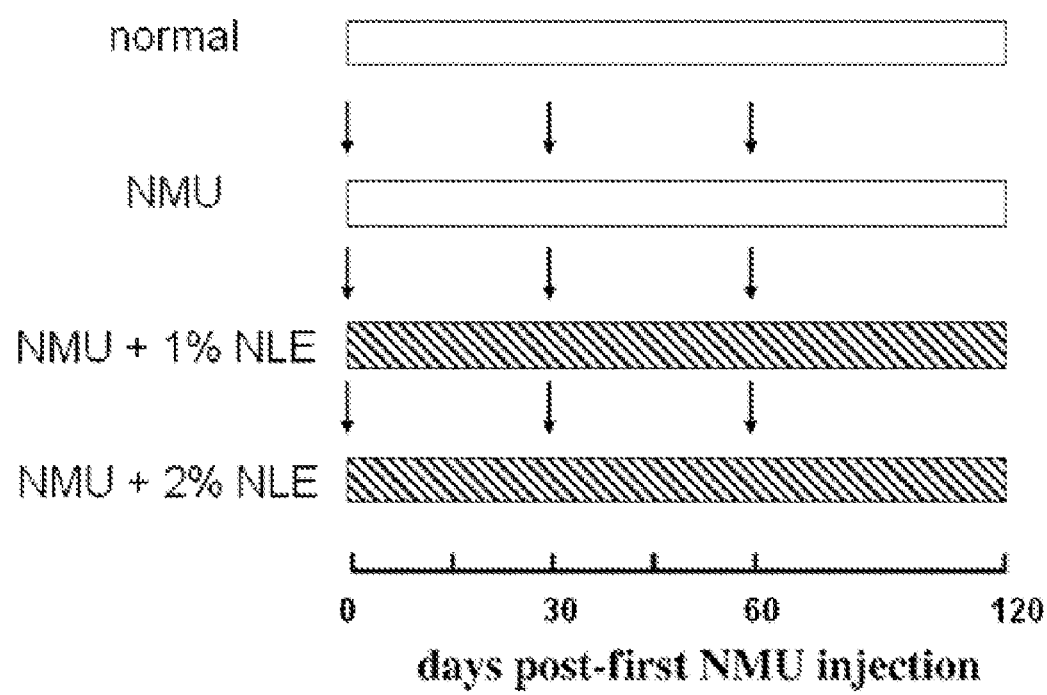
FIG. 1 shows the experimental design for evaluating the chemopreventive effect of *Nelumbo* leaf extract (NLE) against mammary carcinogenesis. The initiating agent, N-nitroso-N-methylurea (NMU), was administered ip (50 mg/kg body weight) at 50, 80, and 110 days of age. Indicated concentration NLE was delivered by gavage daily after first NMU injection. At 120 days the animals were sacrificed. NMU ip; bold lines signify time period of vehicle administration; hatched lines signify time period of NLE administration. NMU, NMU injected group as positive control; NMU+1% NLE, low-dose NLE treated group; NMU+2% NLE, high-dose NLE treated group.

In order to evaluate the chemopreventive effect of NLE against mammary carcinogenesis, the initial agent, NMU (N-nitroso-N-methylurea) which is an effective carcinogen for the induction of mammary carcinoma in rats, was intraperitoneally administered (50 mg/kg body weight) to three groups of rats (10 rats/per group) at 50, 80 and 100 days of age. Low dose of NLE (1% NLE) and high dose of NLE (2% NLE) were delivered to different rats by gavage daily after first NMU injection. At 120 days the rats were sacrificed and the number, size or volume of tumors were measured. NMU injected group without NLE administration was used as positive control. (FIG. 1)

Low dose of NLE (1% NLE) and high dose of NLE (2% NLE) were injected alone with NMU to another two groups of rats to demonstrate the effect of NLE on the mammary carcinoma in rats.

Suppression of NMU-Induced Incidence of Mammary Tumor in Rats by Treatment with NLE In order to analyze the effect of NLE on the mammary carcinoma in rats, rats were separated into four groups (10 rates/per group) for the experiment. Three groups of rats were intraperitoneally administered (50 mg/kg body weight) at three individual time, which was 50, 80 and 100 days after rat's birth, to induce mammary tumor.

Figure 2:
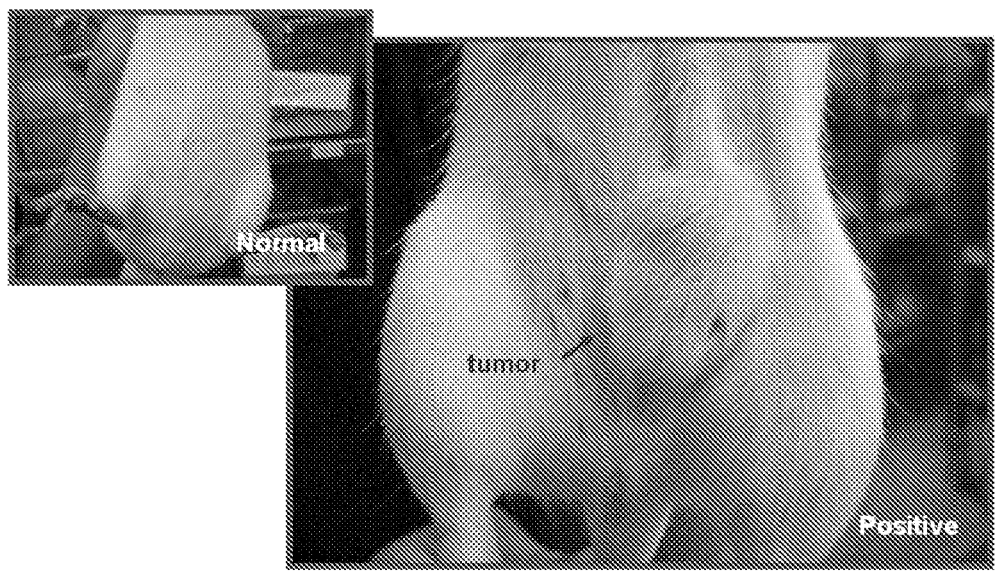
FIG. 2(A) shows a control normal rat and an experimental rat with NMU-induced incidence of mammary tumor.
FIG. 2(B) shows the suppression effect of NLE on the NMU-induced incidence of mammary tumors in rats.
Figure 2:
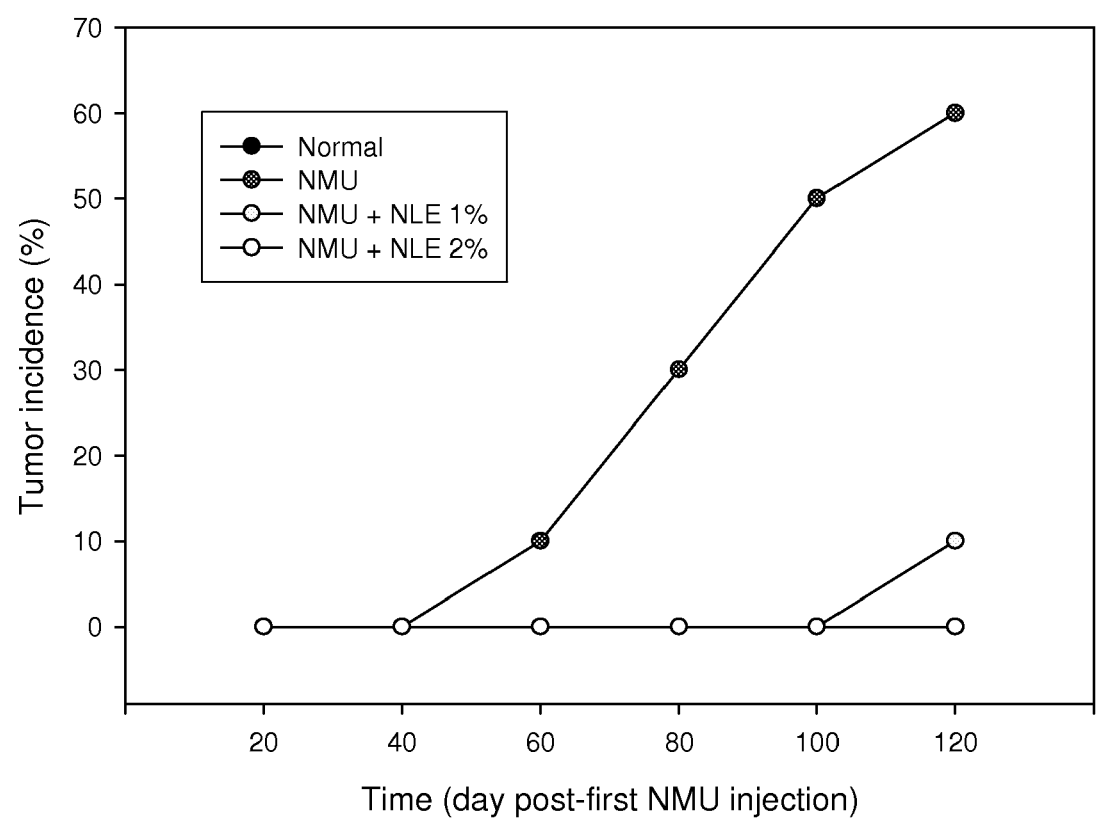

The other one group which was not injected with NMU remained normal. The four groups of mouse were treated with different concentrations of NLE accordingly. The NMU injected group without treatment of NLE was used as positive control; NMU injected group with oral administration of 1% NLE represented low-dose treatment; NMU injected group with oral administration of 2% NLE was high-dose treatment groups. The progressive percentage incidence of cumulative palpable mammary tumors was measured as a function of time after carcinogen treatment (FIG. 2). The result showed that tumor incidence of NMU-induced mammary tumor was suppressed by NLE treatment, and the high does of NLE treatment was more effective than low-dose of NLE treatment on mammary tumor suppression after 100 days of post-first NMU injection.

Figure 3:
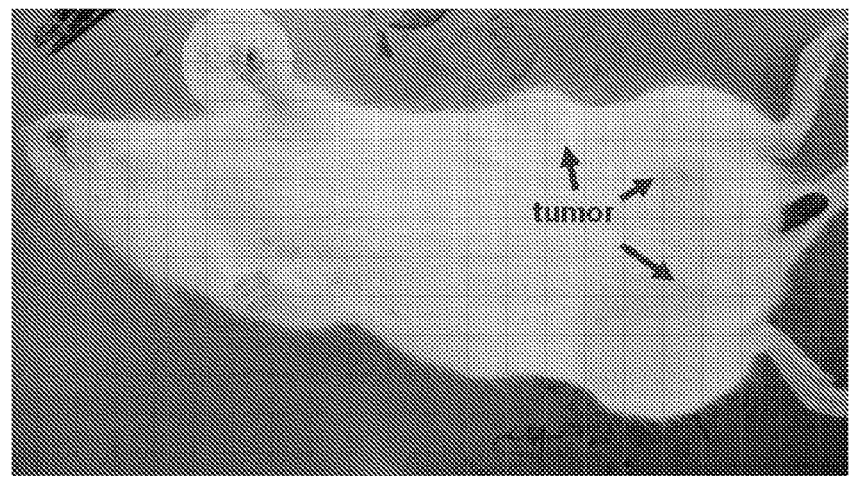
FIG. 3(A) shows a rat with NMU-induced mammary tumor.
FIG. 3(B) shows that NLE injection reduces the mammary tumor number in rats and high dose-of NLE (NLE 2%) is more effective in suppressing tumor number than that of low dose of NLE (NLE 1%).
Figure 3:
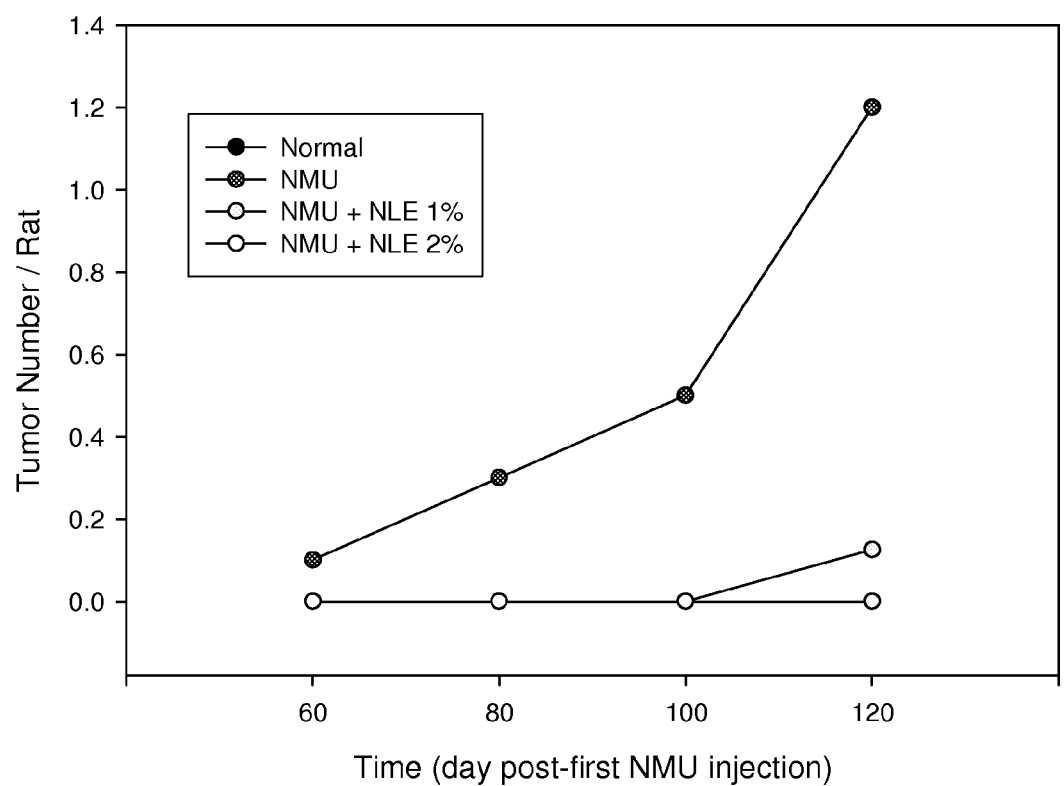

Suppression of NMU-Induced Mammary Tumor Multiplicity in Rats by Treatment with NLE The effects of NLE on suppression tumor multiplicity of NMU-induced mammary tumors were measured by intraperitoneally injecting 3 groups of rats with three doses of NMU (50 mg/kg body weight) at 50, 80 and 110 days of age. All rats were examined by palpation three times a week up to 120 days post-first NMU injection to detect mammary tumors (FIG. 3). The result showed that NMU-induced mammary tumor numbers decreased after the treatment with NLE. This result proved that NLE suppressed tumor multiplicity of NMU-induced mammary tumor effectively.

Suppression of NMU-Induced Mammary Tumor Volume in Rats by Treatment with NLE

Figure 4:
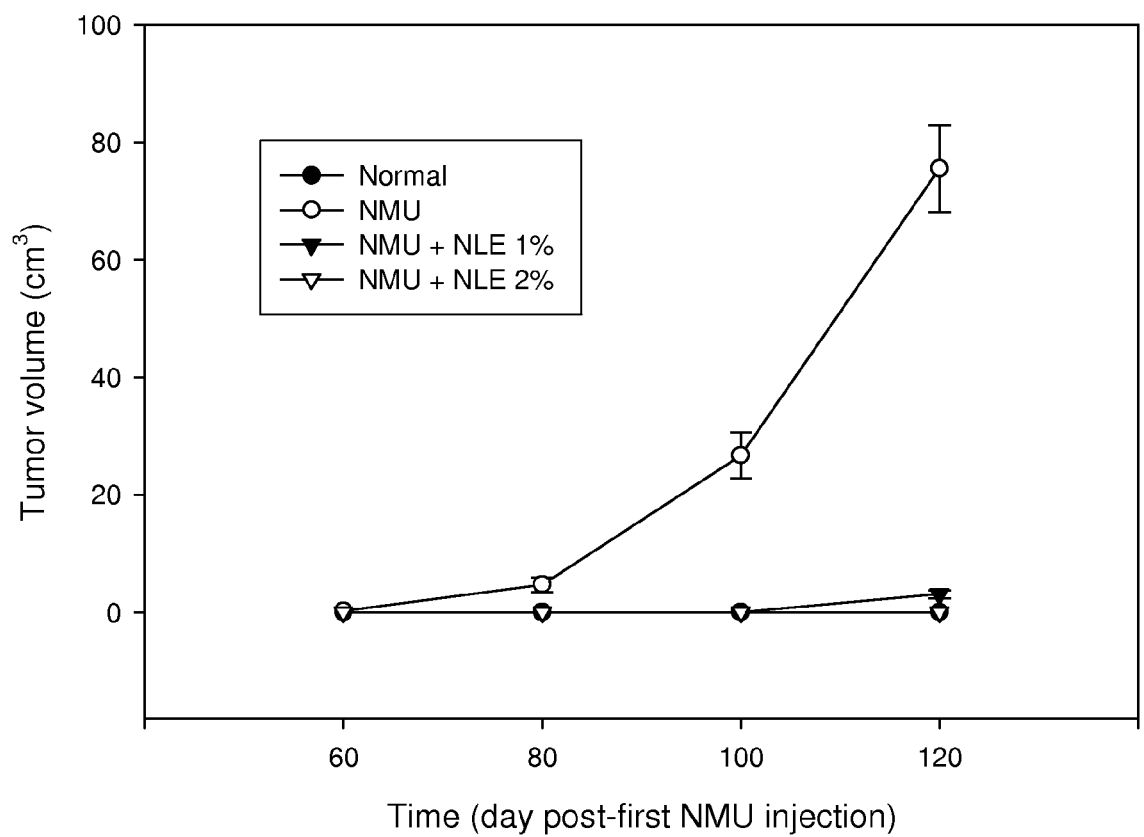
FIG. 4 shows that treatment with NLE suppresses tumor volume of NMU-induced mammary tumor in rats and high dose-of NLE (NLE 2%) is more effective in suppressing tumor number than that of low dose of NLE (NLE 1%).

In order to determine the tumor suppression effect NLE had on the NMU-induced mammary tumor, three groups of rates were intraperitoneally injected with three does of NMU (50 mg/kg body weight) at 50, 80 and 110 days of age and two groups of rats were further injected with 1% NLE and 2% NLE respectively. All rats were examined by palpation three times a week up to 120 days post-first NMU injection to detect the volume of mammary tumors (FIG. 4). The result showed that treatment with NLE could effectively suppress tumor volume of NMU-induced mammary tumors.

Elicitation of Anti-Tumor Effects in Nude Mice by NLE

Figure 5:
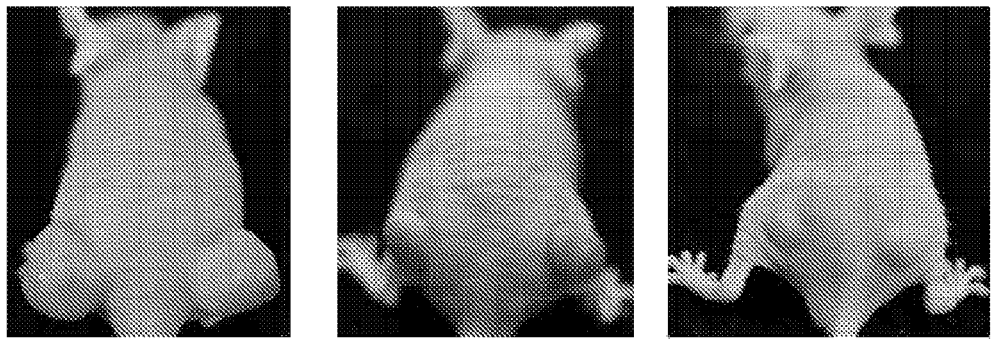
FIG. 5(A) shows the anti-tumor effect NLE has on MCF-7 (Human breast adenocarcinoma) inoculated nude mice.
FIG. 5(B) shows that NLF significantly reduces tumor volume of MCF-7-cell-inoculated nude mice.
Figure 5:
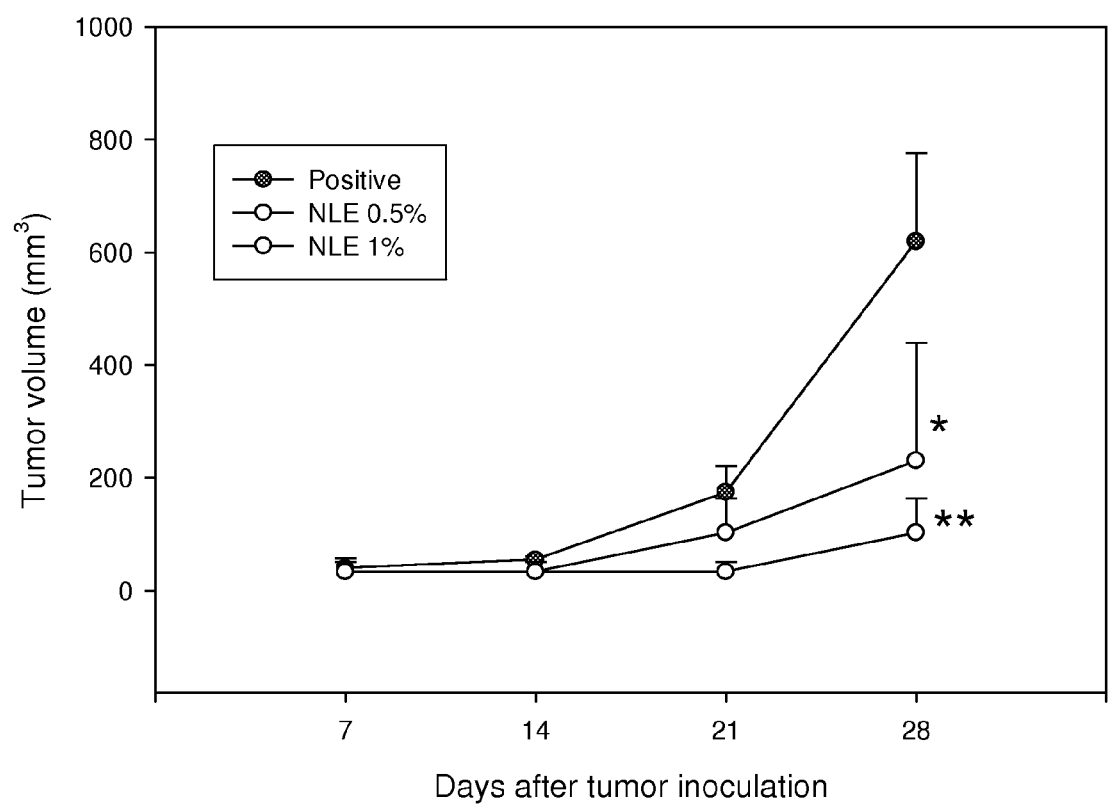

In order to determine whether NLE has anti-tumor elicitation effect, 3 groups of mice were inoculated with MCF-7 (Human breast adenocarcinoma) cells individually by injecting MCF-7 cells into both flanks of each mouse (n=4 per group), and two groups of mice were further orally administrated with 0.5% and 1% NLE/per day respectively. Then, tumor growth was monitored over time. Mice were killed by cervical dislocation and tumors were collected for analysis. The result showed that the tumor size of mouse treated with NLE 1% was smaller than the positive control which meant that NLE elicited anti-tumor effects in nude mice. It is proved that NLE injection decreased the tumor volume in the MCF-7-inoculated mice (FIG. 5).

Suppression of Tumor Growth in Nude Mice by NLE

Figure 6:
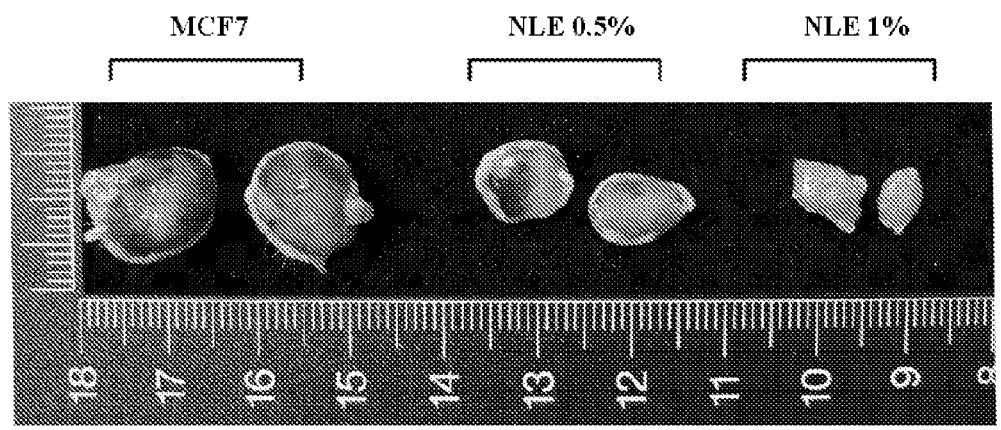
FIG. 6(A) shows the tumors from tree groups of MCF-7-cell-innoculated nude mice dissected at the $28^{th}$ day of inoculation. Three groups of tumor are from NLE absent, NLE 0.5% and NLE 1% mice respectively.
FIG. 6(B) shows that NLE significantly suppresses tumor growth in MCF-7-cell-inoculated nude mice.
Figure 6:
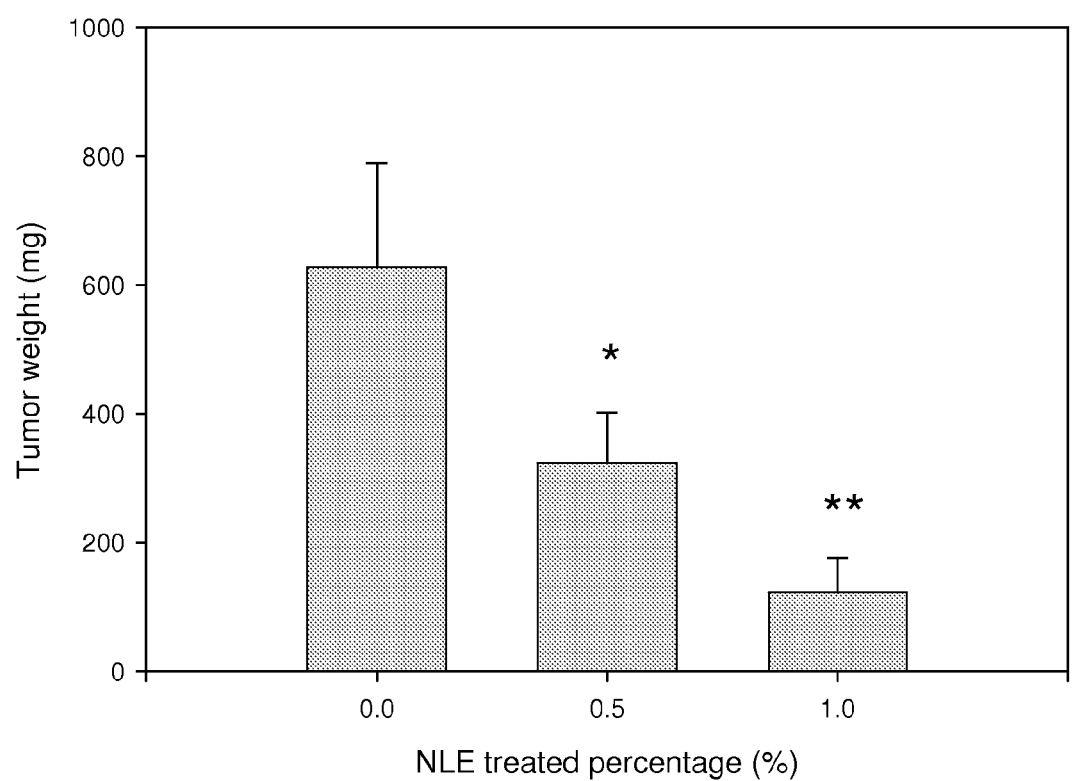

MCF-7 cells were injected subcutaneously into 3 groups of mice (n=4 per group), and two groups of mice were orally administrated daily with 0.5% NLE and 1% NLE respectively. 28 days after injection, mice were killed by cervical dislocation and tumors were collected for analysis. The result showed that tumor weight decreased with NLE treatment which proved that NLE could suppress mammary tumor growth in nude mice. Densitometry analysis of tumor size of each group is shown in FIG. 6.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. Modifications therein and other uses will occur to those skilled in the art. These modifications are encompassed within the spirit of the invention and are defined by the scope of the claims.

What is claimed is:

1. A method for treating breast cancer in a subject suffering therefrom, comprising administrating to the subject a pharmaceutically effective dosage of a *Nelumbo nucifera* leaf extract which is prepared by the following steps:
    (a) cutting *Nelumbo nucifera* leaves into small pieces and extracting with water;
    (b) filtering the extracts through a filter paper;
    (c) concentrating the filtrate by evaporation; and
    (d) lyophilizing the concentrate to yield *Nelumbo nucifera* leaf extract.

2. The method of claim 1, wherein the effective dosage reduces incidence, multiplicity, number, weight, size or volume of mammary tumors in a mammal.

3. The method of claim 1, wherein the effective dosage is 0.1~5% Nelumbo leaf extract.

4. The method of claim 3, wherein the effective dosage is 0.5~2% Nelumbo leaf extract.

5. The method of claim 1, wherein the extract is administrated orally.

6. The method of claim 1, wherein the subject is human.

* * * * *